United States Patent [19]

Bell et al.

[11] Patent Number: 5,244,676
[45] Date of Patent: Sep. 14, 1993

[54] MODIFIED TISSUE PLASMINOGEN ACTIVATOR WITH MODIFIED GLYCOSYLATION SITE

[75] Inventors: Leslie D. Bell, Chesterfield; Ernest J. Mayer, St. Louis; Mark O. Palmier, Webster Groves; H. Eser Tolunay, Creve Coeur; Thomas G. Warren, Ballwin; Tze-Chein Wun, St. Louis, all of Mo.

[73] Assignee: Monsanto Company, St. Louis, Mo.

[21] Appl. No.: 203,047

[22] Filed: Jun. 6, 1988

Related U.S. Application Data

[63] Continuation-in-part of Ser. No. 107,708, Oct. 19, 1987, abandoned.

[51] Int. Cl.$^5$ .................. C12N 9/48; C12N 15/58; C12P 21/02; A61K 37/547
[52] U.S. Cl. .................. 424/94.64; 435/212; 435/219; 435/226; 435/241.2; 435/320.1; 536/23.2; 524/94.63
[58] Field of Search .................. 424/94.64; 435/172.3, 435/212, 226, 240.2, 320; 536/27; 935/10, 14, 24, 27, 32, 60, 70,

[56] References Cited

U.S. PATENT DOCUMENTS 5,149,533  9/1992  Mulvihill et al. ................ 424/94.63

FOREIGN PATENT DOCUMENTS

| 178105 | 4/1986 | European Pat. Off. . |
| 207589 | 4/1986 | European Pat. Off. . |
| 196920 | 10/1986 | European Pat. Off. . |
| 213794 | 3/1987 | European Pat. Off. . |
| 227462 | 7/1987 | European Pat. Off. . |
| 234051 | 9/1987 | European Pat. Off. . |
| 238304 | 9/1987 | European Pat. Off. . |
| 242836 | 10/1987 | European Pat. Off. . |
| 48378 | 3/1987 | Japan . |
| 8601538 | 3/1986 | PCT Int'l Appl. . |
| 8703906 | 7/1987 | PCT Int'l Appl. . |
| 2173804 | 10/1986 | United Kingdom . |

OTHER PUBLICATIONS

Harris, T. J. R., Protein Engineering, 1(6), pp. 449-458, 1987.
Gething, M. J. et al., EMBO Journal, 7(9): 2731-2740, 1988.
Pennica et al., Nature 301, 214-221 (1983).
Vehar, Bio/Technology 2(12), pp. 1051-1057 (1984).
Kagitani et al., FEBS Lett. 189(1), 145-149 (1985).
Zonneveld et al., Proc. Natl. Acad. Sci. USA 83, 4670-4 (1986).
Verheijen et al., The EMBO J. 5(13), 3525-3530 (1986).
Ehrlich et al., Fibrinolysis 1, 75-81 (1987).
Klausner, Bio/Technology 4, 706-711 (1986).
Klausner, Bio/Technology 5, 869-870 (1987).
Lau et al., Bio/Technology 5(9), 953-958 (1987).

Primary Examiner—Robert J. Hill, Jr.
Assistant Examiner—Marianne Porta
Attorney, Agent, or Firm—Scott J. Meyer

[57] ABSTRACT

A modified t-PA having improved in vivo half-life is disclosed comprising in sequence a fibronectin finger-like domain F, a growth factor domain GF, a sequence of two K2 kringle regions and a serine protease region SP, wherein the first of said kringles is free of any glycosylation site and the second of said kringles has a single glycosylation site.

9 Claims, 13 Drawing Sheets

FIG. 1A.

```
                                                                              Nco I
TAACGGTCTCTGCTTACAGAGGTACCCACTCGTTAACTGAATCTGGTCTTCCTCTGTTGCCATGGAACTCTATGATCTTGA 640
ATTGCCAAGAGACGAATGTCTCCATGGGTGAGCAATTGACTTAGACCACGAAGCTACCTTGAGATACTAGAACT

TTGGTAAGGTCTACACCGCTCAAAACCCATCTGCTCAAGCCTTGGGTTGGTAAGCACAACTACTGTAGAAACCCAGAC 720
AACCATTCCAGATGTGGCGAGTTTGGGTAGACGAGTTCGGAACCCAAACCATTCGTGTTGATGACATCTTTGGGTCTG

GGTGACGGCTAAGCCTTGGTGTCTCACGTTTGAAGAACAGAGTCTTACTTGGAGTACTGTGACGTTCCCAGCTGTTCTAC 800
CCACTGCCGATTCGGAACCACAGTGCAAAACTTCTTGTCTGCAGAATGAACCTCATGACACTGCAAGGTCGACAAGATG

CTGTGGTTTCAGACAATACTCTCAACCACACAATTCAGAATTAAAGGTGGTTATTCGCTGACATCGGAGCCATCCTTGGC 880
GACACCAAACTCTGTTATGAGAGTTGGTGTTAAGTCTTAATTCCACCAATAAGCGACTGTAGCCGCTCGGTAGGAACCG

Bgl II
AAGCTCCATCTTCGCCAAGCACAGAGATCTCCAGTGAAAGATTCTGTGTGGTATTTGATCAGCTCTTGTTCC 960
TTCGACGGTAGAAGCGGGTTCGTGTCTTCTAGAGGTCCACTTCTTAAGAACACACCATAAAACTAGTCGAGAACAACC

ATTTTCTCTGCTCCCCACTGTTCCAAGAAGATTCCCACCTCACCATTGACTGTTATCTTGGGTAGAACCTACAGAGT 1040
TAAAACAGACGACGGGTGACAAGGTTCTTTCTAAGGTGGAGTGTAAACTGACAATAGAACCCATCTTGGATGTCTCA

Ava I
CGTTCCCCGGGAAGAGGAACAAAAGTTCGAAGTTGAAAGTACATCGTTCACAAGGAATTTGACGATGACACTTACGACA 1120
GCAAGGGGCCCTTCTCCTTGTTTTCAAGCTTCAACTTTCAAGTTCATGTAGCAAGTGTTCCTTAAACTGCTACTGTGAATGCTGT
```

FIG. 1B.

```
ACGATATCGCTTTGTTACAATTGAGTCTGACTCTTCCAGATGCGGCGCCAAGAATCTTCCGTTCGGCTTAGAACCGTCTGTTTG 1200
TGCTATAGCGAAACATGTTAACTTCAGACTGAGAAGGTCTACGGCGCGGTTCTTAGAAGGCAGCAATCTTGGCAGACAAAC

Sac I
CCACCCGGCCCGACTTGCAATGCCAGACTGGACTGAGCTCTGCTGGTAAGCACGAAGCCTTGCTCTCCATT 1280
GGTGGCCGGGCTGAACGTTACGGTCTGACCTGACTCGAGACGACCATTCGTGCTTCGGAACAGAGGTAA

>Xba I
CTACTCTGAAAGATTGAAGGAAGCTCACGTTAGATGTTACCCATCTTCTAGATGTACCTTCTCAACACTTGTTGAACAGAA 1360
GATGAGACTTTCTAACTTCCTTCGAGTGCAATCTAACATGGGTAGAAGATCTACATGGAAGAGTTGTGAACAACTTGTCTT

CTGTTACCGACAACATGTTGTGCTTGTCTGACACCCCGGTTCTGTGGGCCCCAAGCTAACTTGCACGACGCGTTGTCAAGGT 1440
GACAATGGCTGTTGTACAACACGAACAGACTGTGGGCAAGACACCGGGGTTCGATTGAACGTGCTGCGAACAGTTCCA

CACTCTGGTCGTCCATTGGTCTGTCGTTTGAACGACGTCGAATGACCTTGGTTGGTTGGTATCATTTCTGGGGTTTGTGG 1520
CTGAGACCAGCTAAGGCACCAGAGACAACTTGCTGCCAGCTTACTGGAACCACCATAGTAAAGAACCCAAACCAACACC
                                                                Hind
CCAAAAGGACGTTCCAGGTGTTACACCAAGGTCACCAACTACTTAGACTGGATGATCAGAGAGACAACATGAGACCATAATAA 1600
GGTTTTCCTGCAAGGTCCACAAATGTGGTTCCAGTGGTTGATGAATCTGACCTAGTCTCTGTTGTACTCTGGTATTATTT III BamH I
GCTTG    1600
CGAACCTAG
```

*FIG. 1C.*

```
         M  D  A  M  K  R  G  L  C  C  V  L  L  L  C  G  A
CGATAAGCTTGCAATCATGGATGCAATGAAGAGAGGCTCTGCTGTGTGCTGCTGCTGTGTGGAGCA
TATTCGAAACGTTAGTACCTAAGTTACTTCTCTCCGAGACACAGAGAGACACACCTCGT

V  P  V  S  P  S  Q  E  I  H  A  R  F  R  R  G  A  R-S  Y  Q  V  I
GTCTTCGTTTCGCCCAGCCAGGAAATCCATGCCCGATTCAGAAGAGGAGCCAGATCTTACCAAGTCA
CAGAAGCAAAGCGGGTGGTCCTTAGTACGGGCTAAGTCTTCTCCTCGGTCTGAATGGTTCAGTAT
```

FIG. 2.

```
          GGATCCGGCGATAAGCTTGCAATCATGGATGCAATGAAGAGAGGGCTCTGCTGTGTGCTG
       1  ------------------------------------------------------------ 60
          CCTAGGCCGCTATTCGAACGTTAGTACCTACGTTACTTCTCTCCCGAGACGACACACGAC a:                           MetAspAlaMetLysArgGlyLeuCysCysValLeu -
                               -35
          CTGCTGTGTGGAGCAGTCTTCGTTTCGCCCAGCCAGGAAATCCATGCCCGATTCAGAAGA
      61  ------------------------------------------------------------ 120
          GACGACACACCTCGTCAGAAGCAAAGCGGGTCGGTCCTTTAGGTACGGGCTAAGTCTTCT a:      LeuLeuCysGlyAlaValPheValSerProSerGlnGluIleHisAlaArgPheArgArg -

GGAGCCAGATCTTACCAAGTCATATGTAGAGACGAAAAGACTCAAATGATCTACCAACAA
     121  ------------------------------------------------------------ 180
          CCTCGGTCTAGAATGGTTCAGTATACATCTCTGCTTTTCTGAGTTTACTAGATGGTTGTT a:      GlyAlaArgSerTyrGlnValIleCysArgAspGluLysThrGlnMetIleTyrGlnGln -
                                 +1
          CACCAATCTTGGTTGAGACCAGTTTTGCGTTCTAACAGAGTCGAATACTGTTGGTGTAAC
     181  ------------------------------------------------------------ 240
          GTGGTTAGAACCAACTCTGGTCAAAACGCAAGATTGTCTCAGCTTATGACAACCACATTG

.a:      HisGlnSerTrpLeuArgProValLeuArgSerAsnArgValGluTyrCysTrpCysAsn -

AGCGGCCGCGCTCAATGTCACTCTGTTCCAGTCAAGTCTTGTTCCGAACCAAGATGTTTC
     241  ------------------------------------------------------------ 300
          TCGCCGGCGCGAGTTACAGTGAGACAAGGTCAGTTCAGAACAAGGCTTGGTTCTACAAAG a:      SerGlyArgAlaGlnCysHisSerValProValLysSerCysSerGluProArgCysPhe -

AACGGTGGTACTTGCCAACAGGCCTTGTATTTCTCTGACTTTGTCTGTCAATGTCCTGAG
     301  ------------------------------------------------------------ 360
          TTGCCACCATGAACGGTTGTCCGGAACATAAAGAGACTGAAACAGACAGTTACAGGACTC a:      AsnGlyGlyThrCysGlnGlnAlaLeuTyrPheSerAspPheValCysGlnCysProGlu -

GGTTTTGCTGGTAAGTGTTGTGAAATTGATGGGAATTCTGACTGTTACTTTGGTTCTGGT
     361  ------------------------------------------------------------ 420
          CCAAAACGACCATTCACAACACTTTAACTACCCTTAAGACTGACAATGAAACCAAGACCA a:      GlyPheAlaGlyLysCysCysGluIleAspGlyAsnSerAspCysTyrPheGlySerGly -

TCTGCTTACAGAGGTACCCACTCGTTAACTGAATCTGGTGCTTCCTGTTTGCCATGGAAC
     421  ------------------------------------------------------------ 480
          AGACGAATGTCTCCATGGGTGAGCAATTGACTTAGACCACGAAGGACAAACGGTACCTTG a:      SerAlaTyrArgGlyThrHisSerLeuThrGluSerGlyAlaSerCysLeuProTrpAsn -

TCTATGATCTTGATTGGTAAGGTCTACACCGCTCAAAACCCATCTGCTCAAGCCTTGGGT
     481  ------------------------------------------------------------ 540
          AGATACTAGAACTAACCATTCCAGATGTGGCGAGTTTTGGGTAGACGAGTTCGGAACCCA a:      SerMetIleLeuIleGlyLysValTyrThrAlaGlnAsnProSerAlaGlnAlaLeuGly -

TTGGGTAAGCACAACTACTGTAGAAACCCAGACGGTGACGCTAAGCCTTGGTGTCACGTT
     541  ------------------------------------------------------------ 600
          AACCCATTCGTGTTGATGACATCTTTGGGTCTGCCACTGCGATTCGGAACCACAGTGCAA a:      LeuGlyLysHisAsnTyrCysArgAsnProAspGlyAspAlaLysProTrpCysHisVal -
```

FIG.3A.

```
         TTGAAGAACAGACGTCTTACTTGGGAGTACTGTGACGTTCCCAGCTGTTCTGAAGGTAAC
     601 ---------+---------+---------+---------+---------+---------+ 660
         AACTTCTTGTCTGCAGAATGAACCCTCATGACACTGCAAGGGTCGACAAGACTTCCATTG a:   LeuLysAsnArgArgLeuThrTrpGluTyrCysAspValProSerCysSerGluGlyAsn  -

TCTGACTGTTACTTCGGTAACGGTTCTGCTTACAGAGGTACCCACTCGTTAACTGAATCT
     661 ---------+---------+---------+---------+---------+---------+ 720
         AGACTGACAATGAAGCCATTGCCAAGACGAATGTCTCCATGGGTGAGCAATTGACTTAGA a:   SerAspCysTyrPheGlyAsnGlySerAlaTyrArgGlyThrHisSerLeuThrGluSer  -

GGTGCTTCCTGTTTGCCATGGAACTCTATGATCTTGATTGGTAAGGTCTACACCGCTCAA
     721 ---------+---------+---------+---------+---------+---------+ 780
         CCACGAAGGACAAACGGTACCTTGAGATACTAGAACTAACCATTCCAGATGTGGCGAGTT a:   GlyAlaSerCysLeuProTrpAsnSerMetIleLeuIleGlyLysValTyrThrAlaGln  -

AACCCATCTGCTCAAGCCTTGGGTTTGGGTAAGCACAACTACTGTAGAAACCCAGACGGT
     781 ---------+---------+---------+---------+---------+---------+ 840
         TTGGGTAGACGAGTTCGGAACCCAAACCCATTCGTGTTGATGACATCTTTGGGTCTGCCA a:   AsnProSerAlaGlnAlaLeuGlyLeuGlyLysHisAsnTyrCysArgAsnProAspGly  -

GACGCTAAGCCTTGGTGTCACGTTTTGAAGAACAGACGTCTTACTTGGGAGTACTGTGAC
     841 ---------+---------+---------+---------+---------+---------+ 900
         CTGCGATTCGGAACCACAGTGCAAAACTTCTTGTCTGCAGAATGAACCCTCATGACACTG a:   AspAlaLysProTrpCysHisValLeuLysAsnArgArgLeuThrTrpGluTyrCysAsp  -

GTTCCCAGCTGTTCTACCTGTGGTTTGAGACAATACTCTCAACCACAATTCAGAATTAAA
     901 ---------+---------+---------+---------+---------+---------+ 960
         CAAGGGTCGACAAGATGGACACCAAACTCTGTTATGAGAGTTGGTGTTAAGTCTTAATTT a:   ValProSerCysSerThrCysGlyLeuArgGlnTyrSerGlnProGlnPheArgIleLys  -

GGTGGTTTATTCGCTGACATCGCGAGCCATCCTTGGCAAGCTGCCATCTTCGCCAAGCAC
     961 ---------+---------+---------+---------+---------+---------+ 1020
         CCACCAAATAAGCGACTGTAGCGCTCGGTAGGAACCGTTCGACGGTAGAAGCGGTTCGTG a:   GlyGlyLeuPheAlaAspIleAlaSerHisProTrpGlnAlaAlaIlePheAlaLysHis  -

AGAAGATCTCCAGGTGAAAGATTCTTGTGTGGTGGTATTTTGATCAGCTCTTGTTGGATT
    1021 ---------+---------+---------+---------+---------+---------+ 1080
         TCTTCTAGAGGTCCACTTTCTAAGAACACACCACCATAAAACTAGTCGAGAACAACCTAA a:   ArgArgSerProGlyGluArgPheLeuCysGlyGlyIleLeuIleSerSerCysTrpIle  -

TTGTCTGCTGCCCACTGTTTCCAAGAAAGATTCCCACCTCACCATTTGACTGTTATCTTG
    1081 ---------+---------+---------+---------+---------+---------+ 1140
         AACAGACGACGGGTGACAAAGGTTCTTTCTAAGGGTGGAGTGGTAAACTGACAATAGAAC a:   LeuSerAlaAlaHisCysPheGlnGluArgPheProProHisHisLeuThrValIleLeu  -

GGTAGAACCTACAGAGTCGTTCCCGGGGAAGAGGAACAAAAGTTCGAAGTTGAAAAGTAC
    1141 ---------+---------+---------+---------+---------+---------+ 1200
         CCATCTTGGATGTCTCAGCAAGGGCCCCTTCTCCTTGTTTTCAAGCTTCAACTTTTCATG a:   GlyArgThrTyrArgValValProGlyGluGluGluGlnLysPheGluValGluLysTyr  -
```

*FIG. 3B.*

```
        ATCGTTCACAAGGAATTTGACGATGACACTTACGACAACGATATCGCTTTGTTACAATTG
   1201 ---------+---------+---------+---------+---------+---------+ 1260
        TAGCAAGTGTTCCTTAAACTGCTACTGTGAATGCTGTTGCTATAGCGAAACAATGTTAAC a:      IleValHisLysGluPheAspAspAspThrTyrAspAsnAspIleAlaLeuLeuGlnLeu  -

AAGTCTGACTCTTCCAGATGCGCGCAAGAATCTTCCGTCGTTAGAACCGTCTGTTTGCCA
   1261 ---------+---------+---------+---------+---------+---------+ 1320
        TTCAGACTGAGAAGGTCTACGCGCGTTCTTAGAAGGCAGCAATCTTGGCAGACAAACGGT a:      LysSerAspSerSerArgCysAlaGlnGluSerSerValValArgThrValCysLeuPro  -

CCGGCCGACTTGCAATTGCCAGACTGGACTGAATGTGAGCTCTCTGGTTACGGTAAGCAC
   1321 ---------+---------+---------+---------+---------+---------+ 1380
        GGCCGGCTGAACGTTAACGGTCTGACCTGACTTACACTCGAGAGACCAATGCCATTCGTG a:      ProAlaAspLeuGlnLeuProAspTrpThrGluCysGluLeuSerGlyTyrGlyLysHis  -

GAAGCCTTGTCTCCATTCTACTCTGAAAGATTGAAGGAAGCTCACGTTAGATTGTACCCA
   1381 ---------+---------+---------+---------+---------+---------+ 1440
        CTTCGGAACAGAGGTAAGATGAGACTTTCTAACTTCCTTCGAGTGCAATCTAACATGGGT a:      GluAlaLeuSerProPheTyrSerGluArgLeuLysGluAlaHisValArgLeuTyrPro  -

TCTTCTAGATGTACCTCTCAACACTTGTTGAACAGAACTGTTACCGACAACATGTTGTGT
   1441 ---------+---------+---------+---------+---------+---------+ 1500
        AGAAGATCTACATGGAGAGTTGTGAACAACTTGTCTTGACAATGGCTGTTGTACAACACA a:      SerSerArgCysThrSerGlnHisLeuLeuAsnArgThrValThrAspAsnMetLeuCys  -

GCTGGTGACACCCGTTCTGGTGGGCCCCAAGCTAACTTGCACGACGCTTGTCAAGGTGAC
   1501 ---------+---------+---------+---------+---------+---------+ 1560
        CGACCACTGTGGGCAAGACCACCCGGGGTTCGATTGAACGTGCTGCGAACAGTTCCACTG a:      AlaGlyAspThrArgSerGlyGlyProGlnAlaAsnLeuHisAspAlaCysGlnGlyAsp  -

TCTGGTGGTCCATTGGTCTGTTTGAACGACGGTCGAATGACCTTGGTTGGTATCATTTCT
   1561 ---------+---------+---------+---------+---------+---------+ 1620
        AGACCACCAGGTAACCAGACAAACTTGCTGCCAGCTTACTGGAACCAACCATAGTAAAGA a:      SerGlyGlyProLeuValCysLeuAsnAspGlyArgMetThrLeuValGlyIleIleSer  -

TGGGGTTTGGGTTGTGGCCAAAAGGACGTTCCAGGTGTTTACACCAAGGTCACCAACTAC
   1621 ---------+---------+---------+---------+---------+---------+ 1680
        ACCCCAAACCCAACACCGGTTTTCCTGCAAGGTCCACAAATGTGGTTCCAGTGGTTGATG a:      TrpGlyLeuGlyCysGlyGlnLysAspValProGlyValTyrThrLysValThrAsnTyr  -

TTAGACTGGATCAGAGACAACATGAGACCATAATAAAGCTTGGATCC
   1681 ---------+---------+---------+---------+------- 1727
        AATCTGACCTAGTCTCTGTTGTACTCTGGTATTATTTCGAACCTAGG a:      LeuAspTrpIleArgAspAsnMetArgProEndEnd
```

FIG.3C.

MODIFIED TISSUE PLASMINOGEN ACTIVATOR WITH MODIFIED GLYCOSYLATION SITE

CROSS-REFERENCE TO RELATED APPLICATION

This is a continuation-in-part of copending U.S. application Ser. No. 107,708, filed Oct. 9, 1987, now abandoned.

BACKGROUND OF THE INVENTION

This invention relates to plasminogen activators which are useful thrombolytic agents. More particularly, this invention relates to a modified tissue plasminogen activator having an improved in vivo half-life.

It is known that various plasminogen activators (PA) are widely distributed throughout the body and can be purified from tissue extracts. Typical examples of tissue sources are kidney, lung and uterus tissues. The best characterized of these plasminogen activators fall into two major groups, urokinase plasminogen activator (u-PA) and tissue plasminogen activator (t-PA). u-PA and t-PA are present in ng/ml concentrations in human plasma but are immunologically unrelated. t-PA has been demonstrated to have higher affinity for fibrin than u-PA. u-PA products isolated and purified from human urine and from mammalian kidney cells are pharmaceutically available as thrombolytic agents.

Due to the extremely low concentration of t-PA in blood and tissue extracts, other sources and means of producing this preferred thrombolytic agent have been sought after.

One method of producing t-PA on a large scale comprises isolating the protein from the culture fluid of human melanoma cells grown under in vitro cell culture conditions. An established human melanoma cell line (Bowes) has been used for this purpose. See, for example, European Patent Application 41,766, published Dec. 16, 1981; Rijken and Collen, *J. Biol. Chem.* 256(13), 7035-7041 (1981); and Kluft et al., *Adv. Biotech. Proc.* 2, Alan R. Liss, Inc., 1983, pp. 97-110. The Bowes melanoma t-PA is a glycoprotein which has a molecular weight of about 68,000-70,000 daltons and a 527 amino acid structure with serine at the $NH_2$-terminus. The melanoma t-PA can exist as two chains, an A-chain and a B-chain. It also separates into two variants (or isoforms) in the A-chain, known as types I and II, which differ by about $M_r$ 2000-3000. See Ranby et al., *FEBS Lett.* 146 (2), 289-292 (1982), and Wallen et al., *Eur. J. Biochem.* 132, 681-686 (1983). Type I is glycosylated at Asn-117, Asn-184 and Asn-448 whereas Type II is glycosylated only at Asn-117 and Asn-448 according to Pohl et al., *Biochemistry* 23, 3701-3707 (1984). A high mannose structure has been assigned to Asn-117 whereas two complex carbohydrate structures are assigned to Asn-184 and Asn-448 by Pohl et al., "EMBO Workshop on Plasminogen Activators," Amalfi, Italy, Oct. 14-18, 1985. Genetic information from the Bowes melanoma cell line also has been embodied in *E. coli* by conventional recombinant DNA gene splicing methods to permit the production of the t-PA protein moiety by that microorganism. See, for example, UK Patent Application 2,119,804, published Nov. 23, 1983; Pennica et al., *Nature* 301, 214-221 (1983); and Vehar et al., *Bio/-Technology* 2 (12), 1051-1057 (1984). Recombinant t-PA produced by the expression of Bowes melanoma genetic material in cultured mammalian cells has been administered to humans with some measure of effectiveness. See Collen et al., *Circulation* 70(16), 1012-1017 (1984).

The recombinant-derived t-PA produced in *E. coli* is non-glycosylated and contains only the protein moiety of t-PA. Although the specific function of the carbohydrate moiety on t-PA has not been determined, it is known, in general, that glycosylation can cause certain differences of which the following are of biological interest: antigenicity, stability, solubility and tertiary structure. The carbohydrate side-chains also can affect the protein's half-life and target it to receptors on the appropriate cells. See, for example, Delente, *Trends in Biotech.* 3 (9), 218 (1985), and Van Brunt, *Bio/Technology* 4, 835-839 (1986). The functional properties of carbohydrate-depleted t-PA are further discussed by Little, et al., *Biochemistry* 23, 6191-6195 (1984), and by Opdenakker et al., "EMBO workshop on Plasminogen Activators," Amalfi, Italy, Oct. 14-18, 1985. The latter scientists report that enzymatic cleavage of carbohydrate side-chains from the melanoma (Bowes) derived t-PA by treatment with α-mannosidase causes an increase in the biologic activity of the modified t-PA.

Cultured normal human cells also have been used as a source of t-PA as can be seen from U.S. Pat. Nos. 4,335,215, 4,505,893, 4,537,860, and 4,550,080. Various cell sources mentioned in said patents are primary embryonic (or fetal) kidney, lung, foreskin, skin and small intestines (Flow Laboratories) or the AG1523 cell line. Brouty-Boye et al., *Bio/Technology* 2 (12), 1058-1062 (1984), further disclose the use of normal human embryonic lung cells for the production of t-PA. Rijken and Collen, *J. Biol. Chem.* 256(13), 7035-7041 (1981), and Pohl et al., *FEBS Lett.* 168(1), 29-32 (1984), disclose the use of human uterine tissue as a t-PA source material. European Patent Application 236,289, published Sep. 9, 1987, describes a uniquely glycosylated t-PA derived from normal human colon fibroblast cells.

Production of glycosylated t-PA in non-human mammalian cells also is known. Thus, Kaufman et al., *Mol. Cell. Biol.* 5, 1750-1759 (1985), and European Patent Application 117,059, published Aug. 29, 1984, describe the use of Chinese hamster ovary cells and Browne et al., *Gene* 33, 279-284 (1985), describe the use of mouse L cells for such production. Kaufman et al., state that the Chinese hamster ovary t-PA is glycosylated in a similar but not identical manner as native t-PA. Glycosylated forms of t-PA obtained by recombinant DNA are further described by Zamarron et al., *J. Biol. Chem.* 259 (4), 2080-2083 (1984), and Collen et al., *J. Pharmacol. Expertl. Therap.* 231 (1), 146-152 (1984).

Production of glycosylated t-PA by recombinant DNA yeast cells also has been reported. Thus, European Patent Application 143,081, published May 29, 1985, describes a recombinant yeast plasmid vector which encodes human t-PA from Hela cells. European Patent Application 174,835, published Mar. 19, 1986, describes a t-PA with selected glycosylation expressed in yeast in which the cDNA encoding for the t-PA is derived from Bowes melanoma. European Patent Application 178,105, published Apr. 16, 1986, discloses a glycosylated uterine t-PA expressed in yeast cells or mouse C-127 cells. In the latter case, a bovine papilloma virus is used as the vector.

Notwithstanding the great variety of sources for obtaining t-PA, one of the problems that exists with the normal t-PA molecule is its relatively short half-life. Intravenously administered t-PA disappears rapidly from the circulation into the liver where it is degraded.

The half-life of this clearance is approximately 2 minutes in rabbits [Korninger et al., *Thromb. Haemostas.* 46, 658-661 (1981)]. Recent clinical studies have suggested that the half-life in humans may be slightly longer, on the order of 3-4 minutes [Nilson et al., *Scand. J. Haematol.* 33, 49-53 (1984)]. Since thrombolysis in vivo takes, at best, several hours to achieve, these findings indicate that the successful application of t-PA for thrombolysis in man will require its continuous infusion. Development of a t-PA with a longer half-life would allow for shorter periods of administration or a smaller dose.

Recently, so-called second generation type t-PAs have been prepared by recombinant DNA technology and various protein engineering schemes in attempting to improve the t-PA molecule. It is known that the normal t-PA molecule has five functional domains or regions: A fibronectin-like finger domain F); an epidermal growth factor region (GF); two kringle regions (K1 and K2); and a serine protease region (SP). In the 527 amino acid sequence of the normal t-PA molecule described by Pennica et al., *Nature* 301, 214-221 (1983), the finger region comprises residues 1-43; the growth factor region comprises residues 44-91; kringle refers to a characteristic triple disulfide structure of which t-PA has two such regions, K1—residues 92-173, and K2—residues 180-261; and the serine protease comprises residues 262-527. The SP catalytic site is formed from the His-322, Asp-371 and Ser-478 residues. Various deletions of one or more of these regions together with elimination of one or more of the glycosylation sites such as by site-directed mutagenesis have been described heretofore. See, for example, Kagitani et al., *FEBS Lett* 189(1), 145-149 (1985); Zonneveld et al., *Proc. Natl. Acad. Sci. USA* 83, 4670-4674 (1986); Verheijen et al., *The EMBO J.* 5 (13), 3525-3530 (1986); Ehrlich et al., *Fibrinolysis* 1, 75-81 (1987); Klausner, *Bio/Technology* 4, 706-710 (1986) and 5, 869-870 (1987); and various abstracts in *Thromb. Haemostasis.* 58, 1-676 (1987). European Patent Applications 234,051, published Sep. 2, 1987, and 242,836, published Oct. 28, 1987, and PCT International Application WO 87/03906, published Jul. 2, 1987, disclose a variety of t-PA mutants having alterations in the arrangement of one or more of the functional domains.

Specific examples of t-PA having such domain changes are as follows:

In European Patent Application 196,920, published Oct. 8, 1986, a modified t-PA is described which has the intact B chain of mature t-PA linked to kringle K2 as the only functionally and structurally intact domain of native t-PA A chain. European Patent Application 207,589, published Apr. 2, 1986, describes a t-PA in which all or part of the growth factor region (GF) has been deleted. Japanese Patent KOKAI No. 48378/87, laid open Mar. 3, 1987, discloses an improved t-PA having a part or the whole of the kringle domains deleted. In European Patent Application 213,794, published Mar. 11, 1987, a hybrid t-PA is described which has a plurality of heterologous kringles (2 to 6 kringles), for example, a t-PA protein with a prothrombin or urokinase kringle region. In PCT Inter. Appln. WO 87/03906, several modified t-PAs are disclosed, including one in which the growth factor region (GF) and the first kringle region (K1) have been deleted but which contains an additional second kringle region (K2).

Specific examples of t-PA having various site-directed mutagenesis are as follows:

In European Patent Application 178,105, published Apr. 16, 1986, a modified t-PA is described in which one or more of the glycosylation sites have been eliminated by site-directed mutagenesis of Asn to Gln at the glycosylation sites in the kringle and serine protease regions. The amino acid residues Asn-120, -187 and -451 in the described uterine t-PA are equivalent to residues Asn-117, -184 and -448, respectively, in the Bowes melanoma t-PA. U.K. Patent Application G.B. 2,173,804, published Oct. 22, 1986, describes mutagenesis in the region of residues 270 to 279 to prevent conversion to the two-chain form of t-PA, especially mutagenesis of Arg-275 and Ile-276, e.g. Arg-275 → Gly or Glu. In PCT International Application WO 86/01538, published Mar. 14, 1986, the mutant Lys-227 → Ile is described. A variety of site-mutagens are also described in European Patent Application 227,462, published Jul. 1, 1987, including mutagenesis at the above glycosylation sites and at the cleavage sites in the region 272-280, especially in the sequence Phe(274)-Arg(275)-Ile(276)-Lys(277). Other such mutants are disclosed in European Patent Application 238,304, published Sep. 23, 1987.

BRIEF DESCRIPTION OF THE INVENTION

In accordance with the present invention a novel modified t-PA has been developed with a substantially improved in vivo half-life. The modified t-PA is constructed to comprise in sequence, starting with the N-terminal amino acid, a fibronectin finger-like domain (F), a growth factor domain (GF), a sequence of two K2 kringle regions and a serine protease region (SP). The modified t-PA thus lacks the K1 kringle region of normal t-PA. In addition, the t-PA of this invention is further modified to eliminate the glycosylation site in the first K2 kringle but not in the second K2 kringle of the sequence.

For convenience, the modified t-PA of this invention can be represented as F+GF+K2+K2+SP[Asn(96)→Ser]. This molecule can be constructed from the component parts by recombinant DNA procedures. In a preferred embodiment, the modified t-PA was prepared from a chemically synthesized gene coding for t-PA. The t-PA gene can be represented as F+GF+K1+K2+SP. By making a large restriction enzyme deletion and a small oligonucleotide replacement, a first modified t-PA represented as F+GF+K2+SP[Asn(96)→Ser] was made. Similarly, a separate fragment of t-PA represented as K2 was made. By combining the fragment K2 with the F+GF+K2+SP [Asn(96)→Ser] from the former modified t-PA, the complete modified t-PA of this invention, F+GF+K2+K2+SP[Asn(96)→Ser], was thereby constructed.

In a preferred embodiment of this invention, designated herein as t-PA variant MB1012, the mature protein has a 527 amino acid structure in which residues 1-50 comprise the fibronectin finger-like domain (F), residues 51 to 87 comprise the growth factor domain (GF), residues 88 to 174 comprise the first K2 kringle region, residues 175 to 262 comprise the second K2 kringle region and residues 263 to 527 comprise the serine protease region (SP). In this variant, residues 1-87 correspond to residues 1-87 of the native t-PA, residues 88-174 correspond to residues 176-262 of the native t-PA, except that the glycosylation site corresponding to Asn-184 has been replaced with serine, and residues 175 to 527 correspond to residues 175 to 527 of native t-PA. Thus, the residue Asn-96 in the first K2 kringle of the modified t-PA sequence is replaced with Ser-96, whereas the residue Asn-184 in the second K2 kringle is not thus replaced.

The gene coding for the modified t-PA of this invention can be cloned into and expressed in prokaryotic and eukaryotic hosts. For example, active modified t-PA protein can be expressed in a prokaryotic host such as E. coli or a eukaryotic host such as Chinese hamster ovary (CHO) cells or C-127 mouse cells by operably inserting the modified t-PA coding sequence in replicable expression vectors or plasmids. For example, it can be inserted into a suitable plasmid such as pML2 for production in E. coli and the bovine papilloma virus (BPV) vector for production in mouse cells or a shuttle vector which can replicate in both prokaryotic and eukaryotic cells. In a preferred embodiment, the gene coding for the t-PA sequence F+GF+K2+K2+SP[Asn(96)→Ser] was cloned into and expressed from C-127 mouse cells. The excreted protein was extracted from the cell media by concentration and then purified on an affinity chromatography column.

A preferred cloning vector containing the nucleotide sequence for the t-PA variant MB1012 is plasmid pMON1437. This plasmid carried in a mouse C-127 host cell is on deposit with the American Type Culture Collection, Rockville, Md., under accession number ATCC CRL 9717. Other suitable eukaryotic and prokaryotic hosts for expression of the novel modified t-PA of this invention will be readily apparent to the person skilled in the art after reading the present disclosure.

The modified t-PA of this invention was shown to have a substantially longer half-life ($t_{\frac{1}{2}}$) than native t-PA by injecting radiolabelled t-PA protein into rats. When measured in a plasminogen dependent rate assay or in an in vitro clot lysis assay, the modified t-PA was found to be less active than the native t-PA.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments of the invention in conjunction with the appended drawings, in which briefly:

FIGS. 1A-1C show the construction of a chemically synthesized gene coding for t-PA assembled from individual oligonucleotides (positioned between the < > symbols) with nucleotide sequences and restriction enzyme sites as shown. Nucleotides are numbered on the right-hand side. The 1609 bp DNA is split into Panels A, B and C.

FIG. 2 shows the nucleotide sequence of a synthetic gene fragment which includes the signal sequence of native t-PA. The 35 amino acids coded by the signal sequence beginning with methionine followed by the first 5 amino acids of the mature protein beginning with serine are shown above the nucleotide sequence.

FIGS. 3A-3C show the nucleotide sequence of the t-PA variant MB1012. The nucleotides, which include some upstream and downstream processing, are numbered 1 to 1727. The corresponding amino acid sequence of the t-PA protein is shown below the nucleotide sequence in the rows labelled "a." The signal sequence (as in FIG. 2) begins with the methionine at position −35 while the mature protein of 527 amino acids begins with the serine at position +1.

Figure 5:
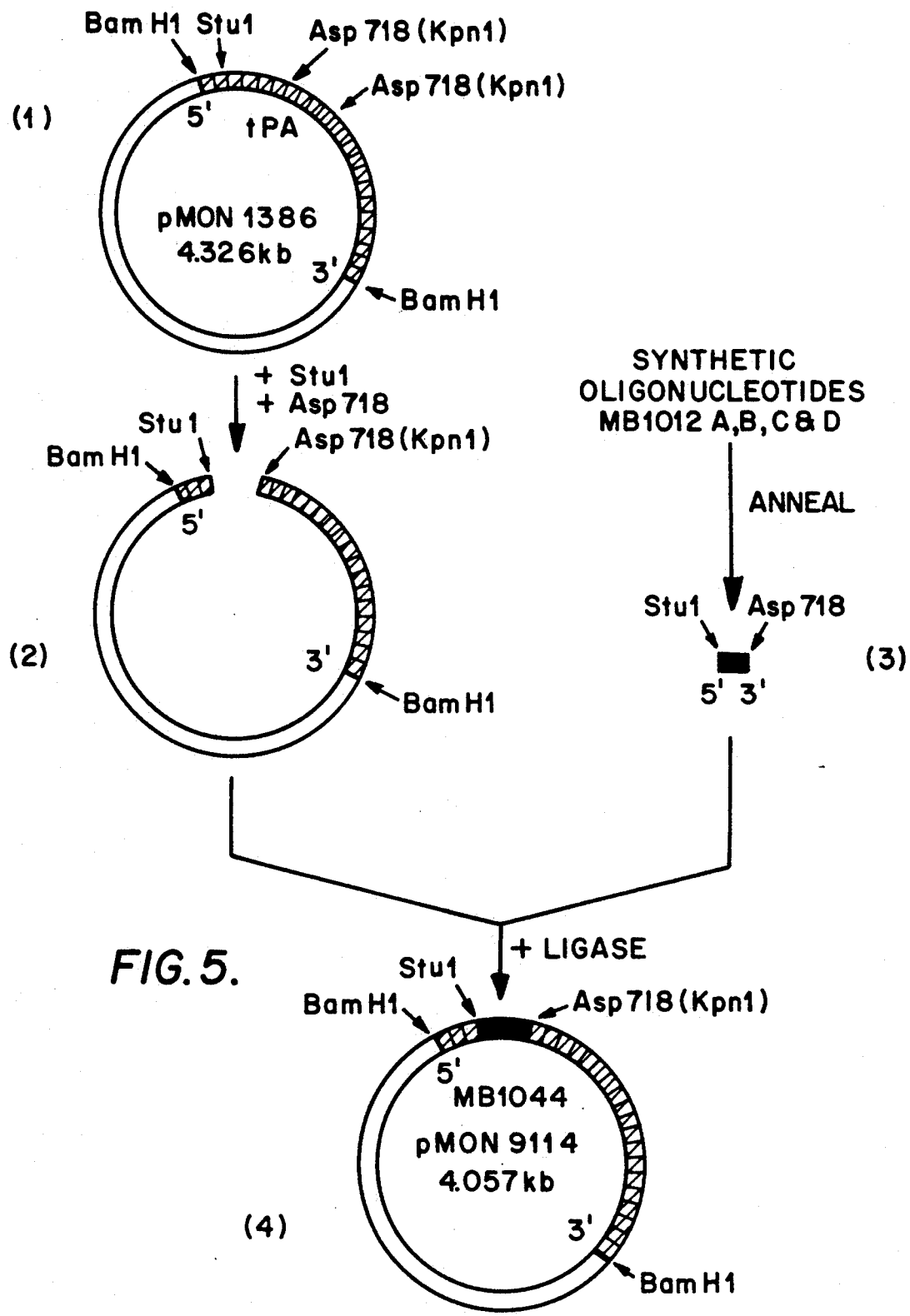
FIG. 5 shows the construction of pMON9114 of 4057 bp from plasmid pMON1386 of 4326 bp of FIG. 4 and synthetic oligonucleotides MB1012 A, B, C, and D.
Figure 6A:
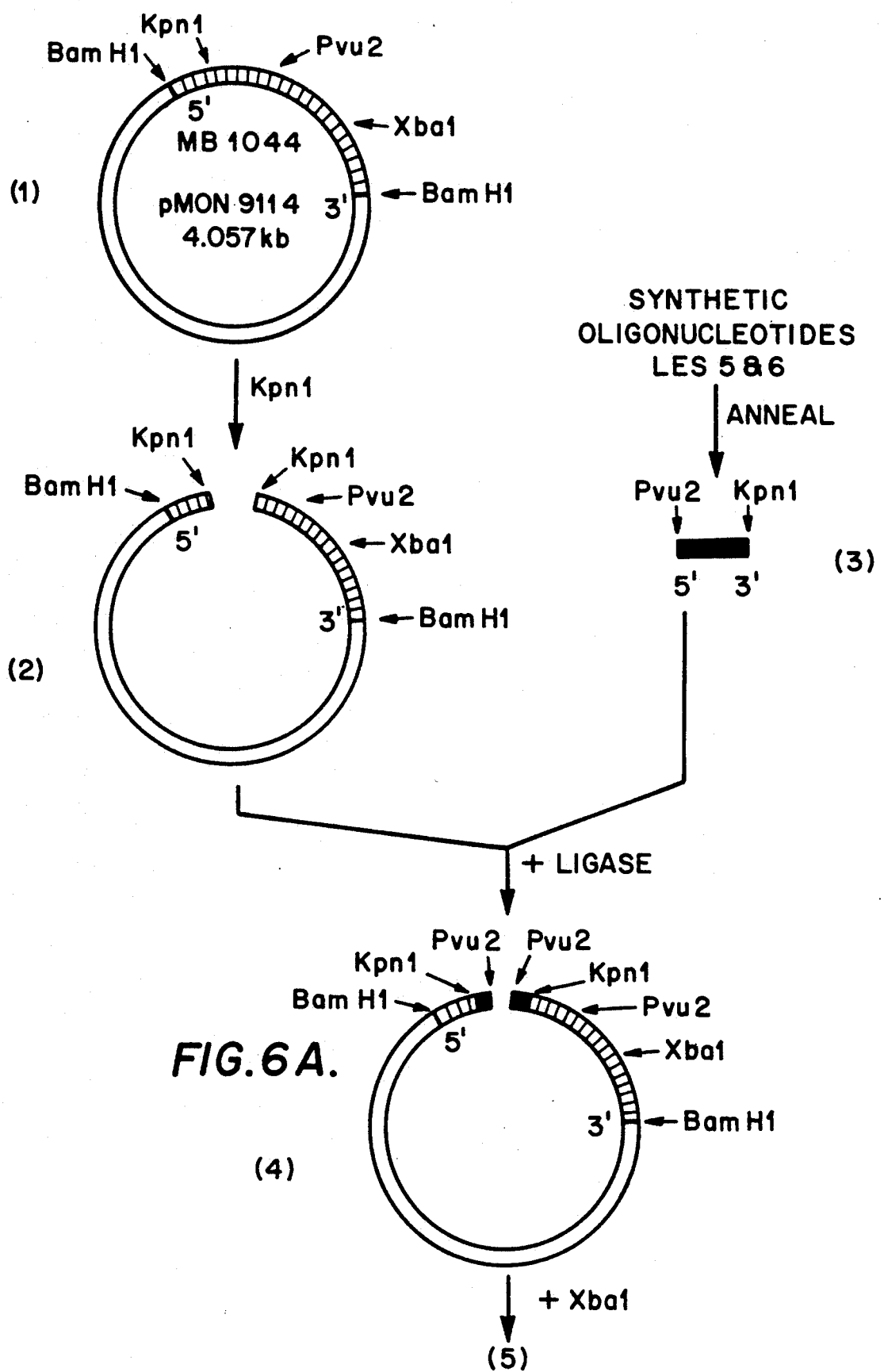
Figure 6B:
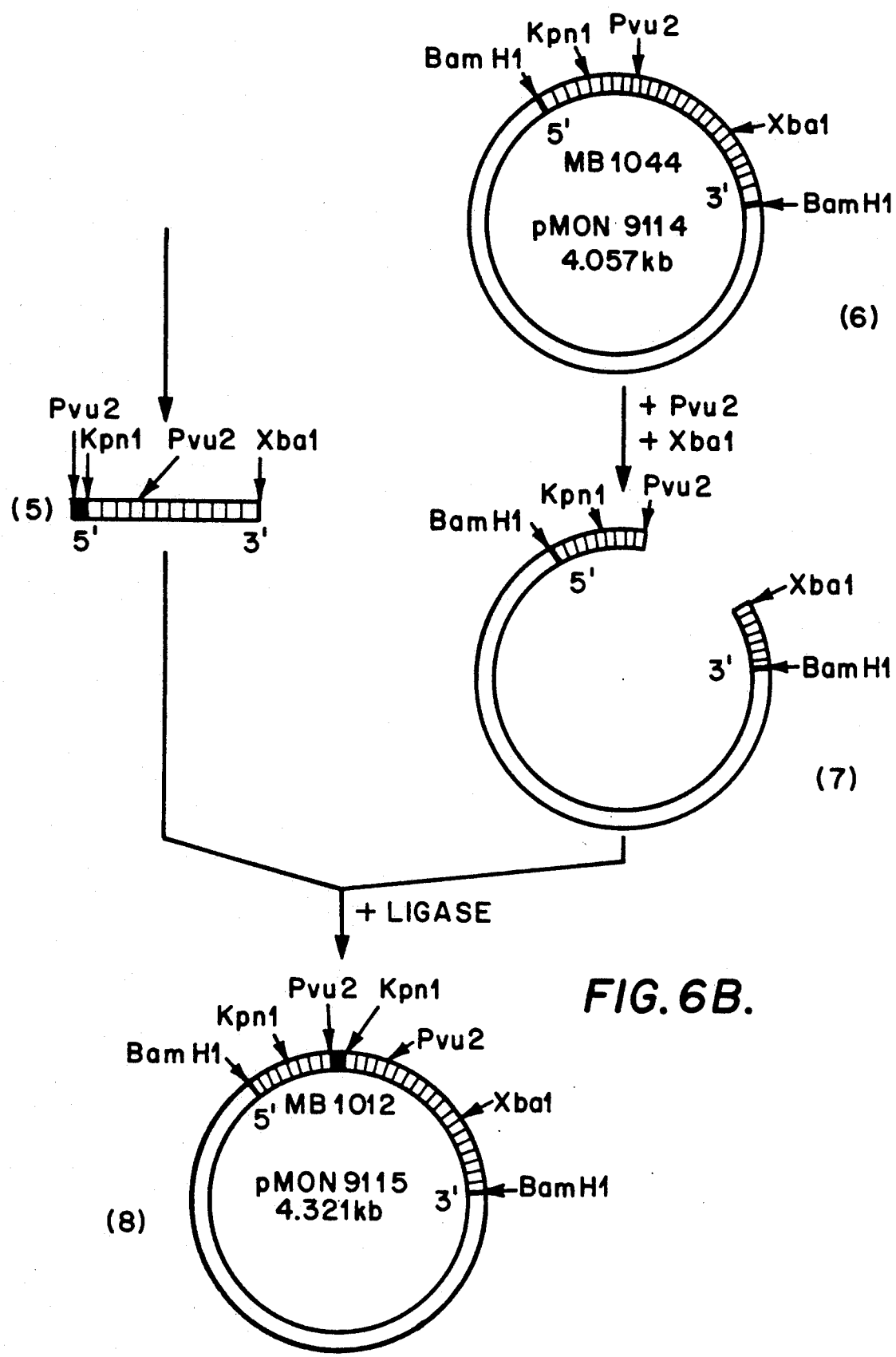

FIGS. 6A and 6B show the construction of pMON9115 of 4321 bp. FIG. 6A shows the digestion of pMON9114 of FIG. 5 with Kpn1 and ligation of fragment 2 with synthetic oligonucleotides LES 5&6 (fragment 3); FIG. 6B shows digestion of pMON9114 of FIG. 5 with Pvu2 and Xba1 and ligation of fragment 7 with fragment 5 obtained in FIG. 6A to yield pMON9115, which contains the complete coding sequence of t-PA variant MB1012.

Figure 7:
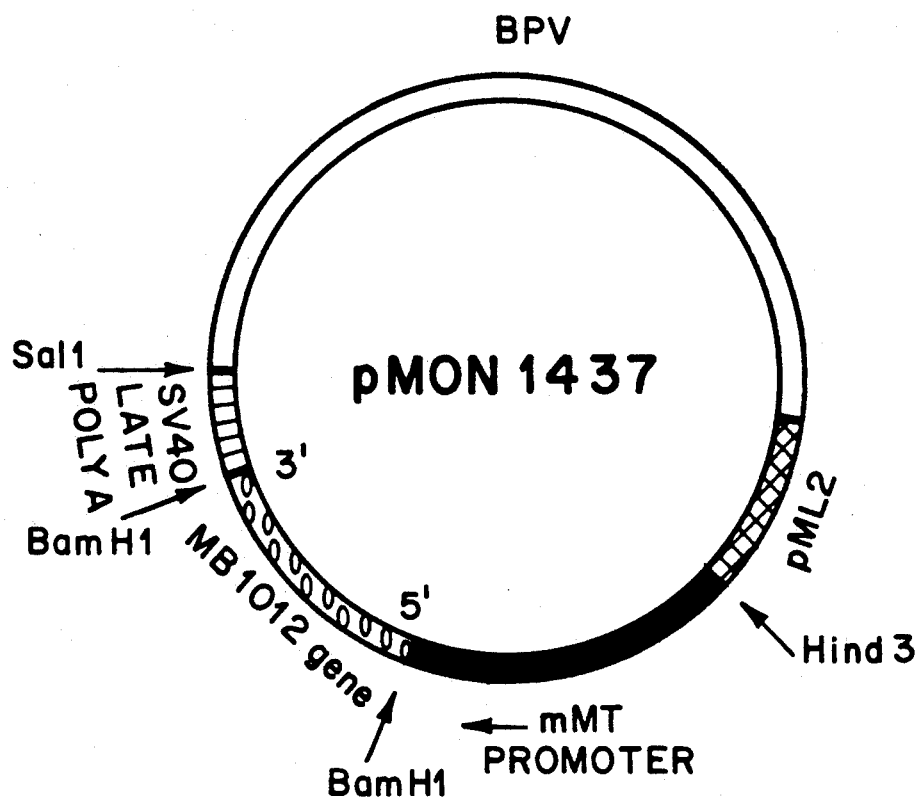

FIG. 7 shows the plasmid pMON1437 which is an expression vector for the expression of t-PA variant MB1012 in mouse C-127 cells in one embodiment of the invention. In this vector, BPV is the complete bovine papilloma virus genome, SV40 is the late poly(A) addition site of the SV40 virus, mMT is the mouse metallothionien I promoter and pML2 is a derivative of the E. coli plasmid pBR322 with an animal viral insert.

Figure 8:
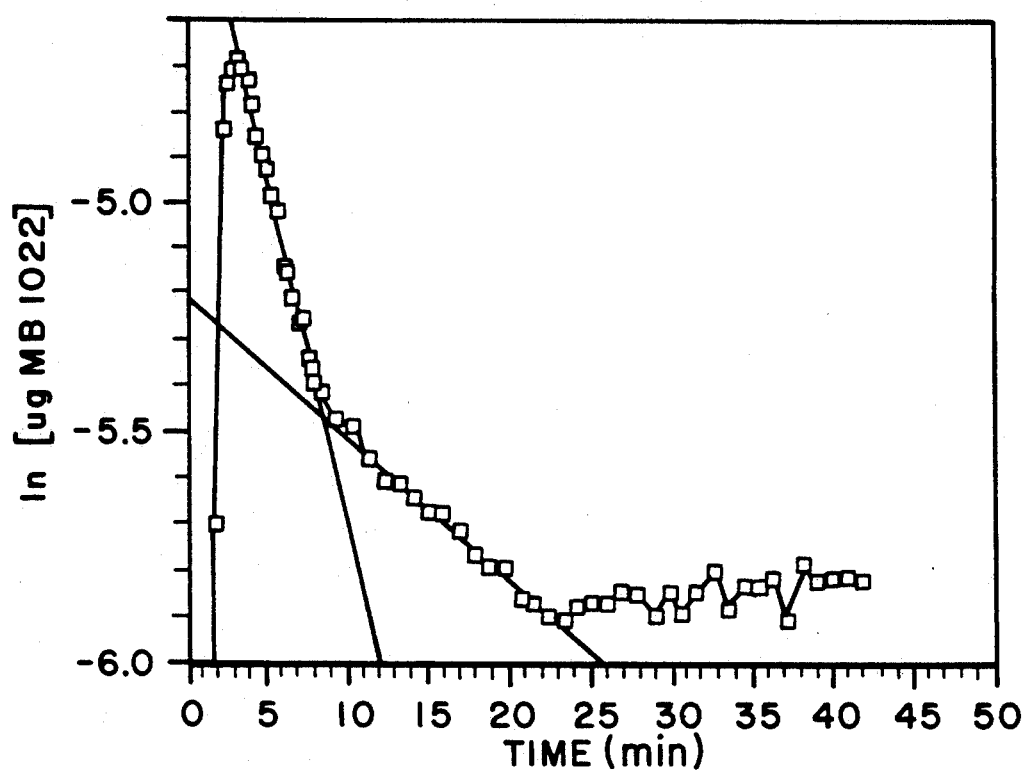

FIG. 8 is a graphical representation which shows the in vivo clearance of Bowes melanoma t-PA (MB1022) in the rat following bolus injection. The half-life ($t_{\frac{1}{2}}$) was calculated by linear regression of ln [μg t-PA] vs. time (minutes).

Figure 9:
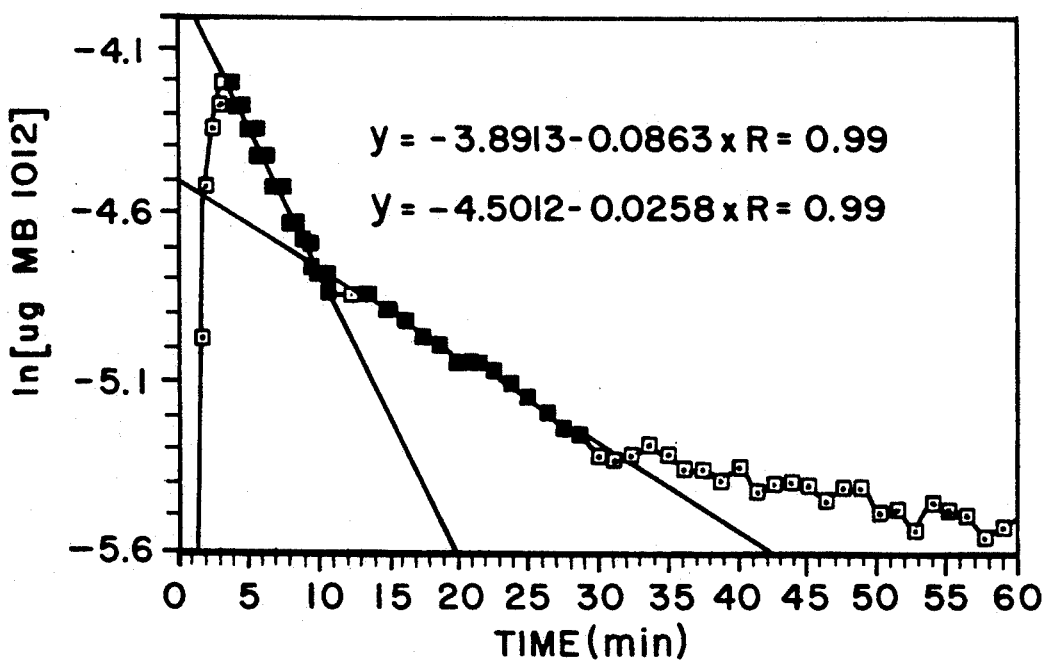

FIG. 9 is a graphical representation which shows the in vivo clearance of t-PA variant MB1012 in the rat following bolus injection. The $t_{\frac{1}{2}}$ was calculated as in FIG. 8.

Figure 1A:
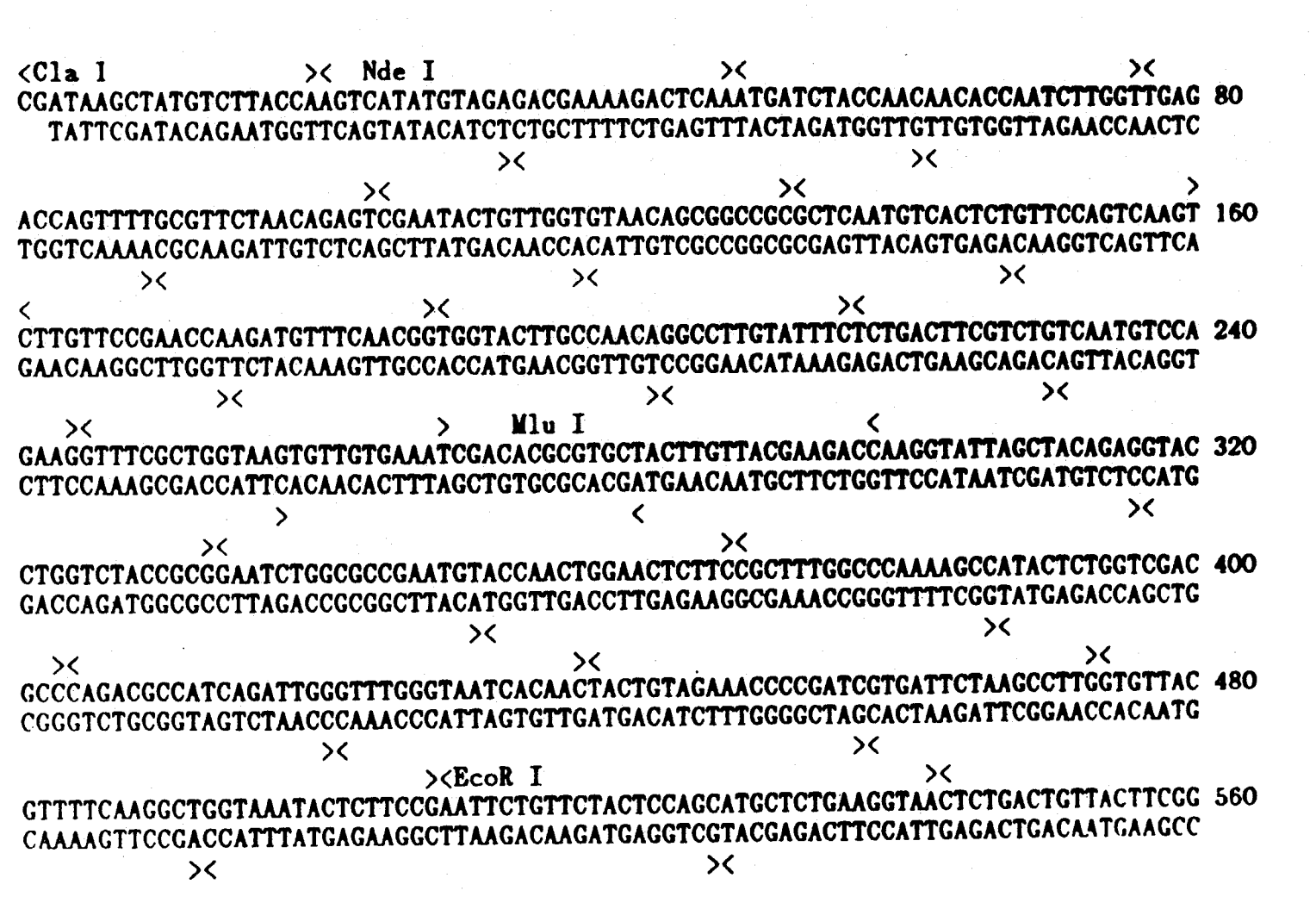
Figure 4:
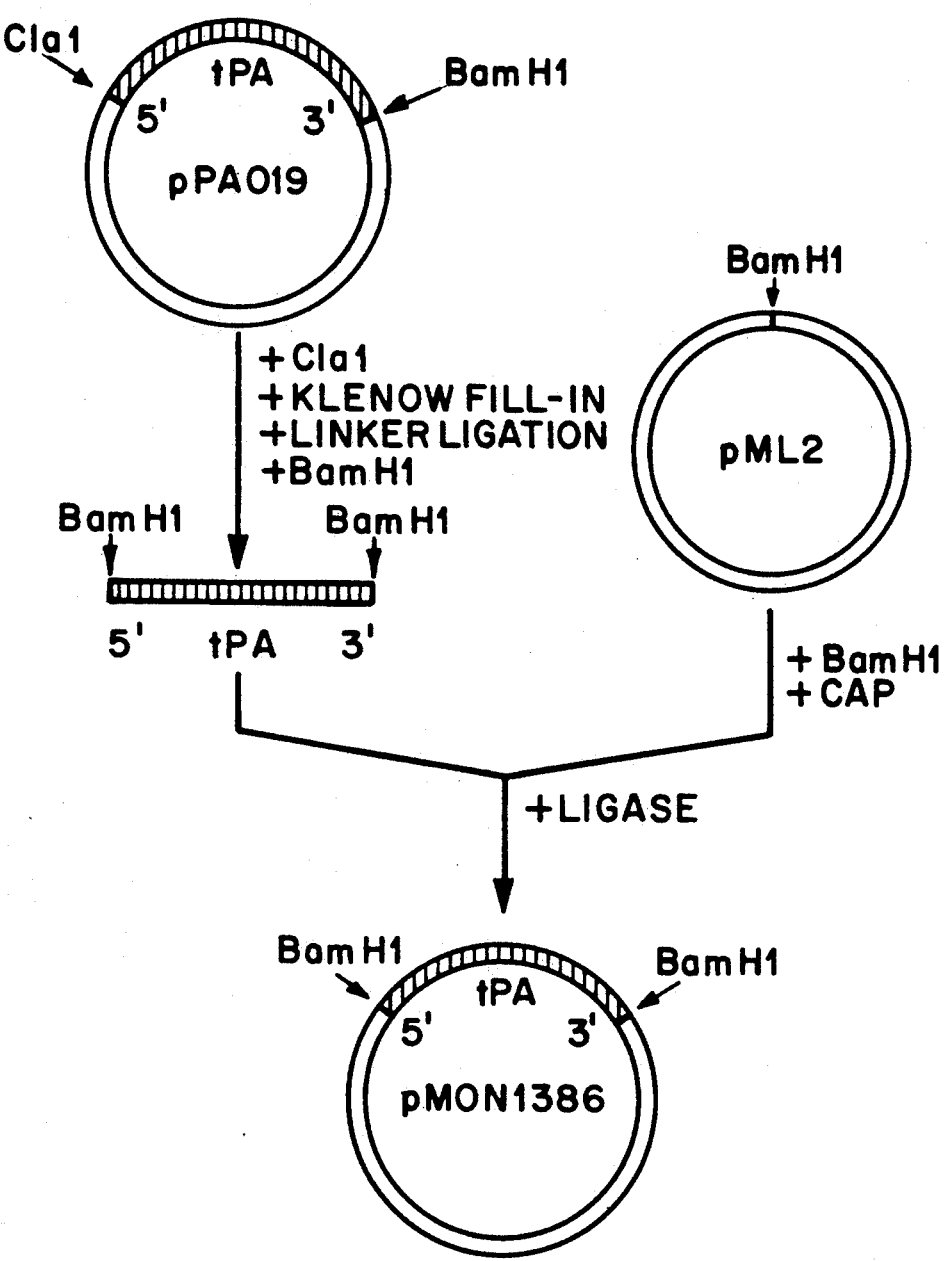
FIG. 4 shows the construction of plasmid pMON1386 of 4326 bp from plasmid pPA019 of 5028 bp and plasmid pML2 of 2600 bp.

The nucleotide sequence of FIGS. 1A -1C and 2, the construction of pMON1386 of FIG. 4, the sequences of synthetic oligonucleotide fragments LES 5&6 and the in vivo clearance of melanoma t-PA MB1022 of FIG. 8 are also shown in co-pending application Ser. No. 107,708, filed Oct. 9, 1987.

Standard biochemical nomenclature is used herein in which the nucleotide bases are designated as adenine (A); thymine (T); guanine (G); and cytosine (C). Corresponding nucleotides are, for example, deoxyadenosine-5'-triphosphate (dATP). Amino acids are shown either by three letter or one letter abbreviations as follows:

| Abbreviated Designation | | Amino Acid |
|---|---|---|
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Commonly available restriction endonucleases used herein have the following restriction sequences and (indicated by arrows) cleavage patterns.

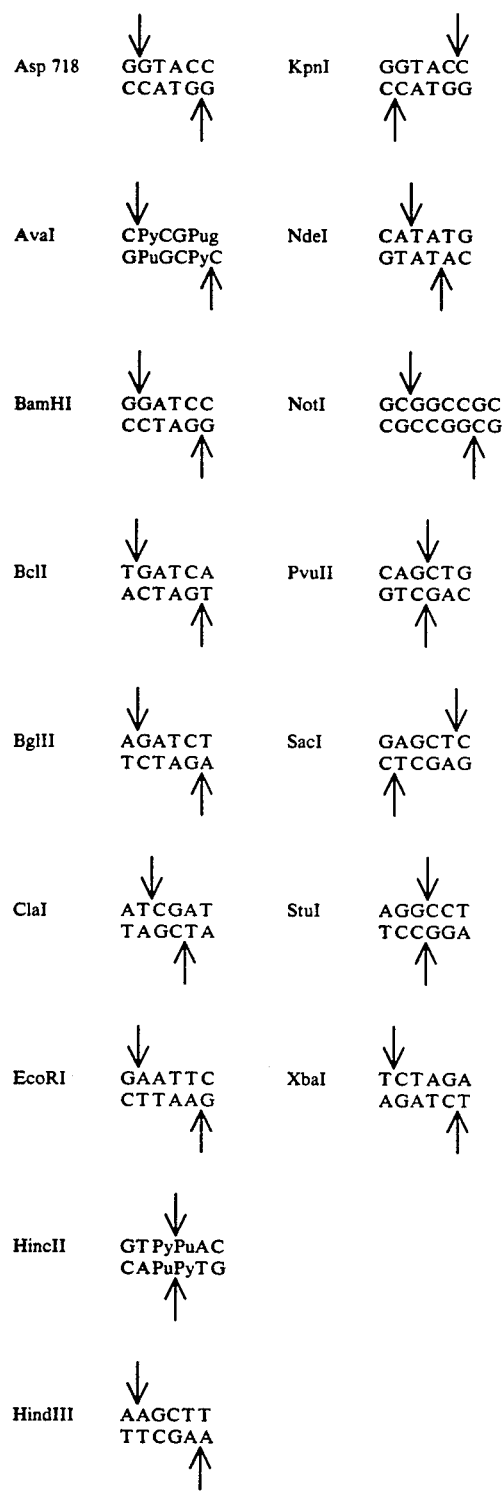

In order to illustrate specific preferred embodiments of the invention in further detail, the following exemplary laboratory work was carried out. This work includes the construction of a chemically synthesized t-PA gene from selected oligonucleotides and cloning of the gene in a suitable plasmid vector. A modified t-PA, variant MB1012, was then constructed by digestion of the t-PA coding sequences with selected restriction enzymes to afford desired DNA fragments. The fragments were isolated and ligated with selected synthetic oligonucleotides and introduced into an appropriate plasmid vector for cloning and subsequent expression of a 527 amino acid modified t-PA having the protein sequence represented by F-GF-K2-K2-SP[Asn(9-6)→Ser].

EXAMPLES

Construction of MB1012

Materials

Enzymes were obtained from New England Biolabs, Boehringer Mannheim Biochemicals or Sigma Chemical Company and used according to the manufacturers printed specifications. Chemicals and components of media were obtained from Sigma Chemical Company and American Scientific Products, respectively. 5'-Dimethoxytritylated N-protected nucleosides were purchased from Cruachem. T4 DNA ligase and T4 polynucleotide kinase were obtained from Amersham International. Controlled pore glass (CPG, 700 Å pore size, 200–400 mesh) was purchased from BDH.

Methods

Construction of Synthetic t-PA Gene

A synthetic t-PA gene was designed as shown in FIG. 1. The codon choice was based on optimum yeast codons, but also includes many restriction endonuclease sites. The gene was divided into oligonucleotides as shown, for the purpose of chemical synthesis.

Preparation of Ligonucleotides

Aminopropyl CPG was prepared as described by Chow et al., Nucleic Acids Research 9, 2807–2817 (1981). 5'-Dimethoxytrityl deoxyribonucleoside 3'-O-succinates were synthesized and coupled to aminopropyl CPG following published procedures [Chow et al., Ibid.]. Methyl phosphodichloridite was prepared by the method of Martin and Pizzolato, J. Amer. Chem. Soc. 72, 4584–4586(1950). 5'-Dimethoxytrityl-deoxyribonucleoside-3'-O -(N,N-diisopropylamino)-methyl phosphoramidites were prepared by a modification of the method of McBride and Caruthers, Tetrahedron Letters 24, 245–248 (1983). Products were precipitated from pentane at −20° C. and used without further purification. Phosphoramidites were stored at room temperature in a dry atmosphere. Oligonucleotides were prepared using an automated synthesizer. Syntheses were carried out in glass columns (bed volume: 6.5 mm I.D.×50 mm, Omnifit) containing 50 mg of derivatized CPG (25 μmole nucleotide/g). After each addition the yield was estimated by spectrophotometric assay of the acid-cleaved dimethoxytrityl cation. At the end of the synthesis the 5'-dimethoxytrityl group was removed by treatment with 3% dichloroacetic acid in dichloromethane. Other protecting groups were removed by treatment with thiophenol-dioxane-triethylamine (1:2:1) for 60 minutes at room temperature, followed by treatment with concentrated ammonia in a sealed vial at 70° C. for 4 hours.

Purification of Oligonucleotides

Deprotected oligonucleotides were precipitated from concentrated ammonia by the addition of 0.1 volume of 3M sodium acetate (pH 5.2) and 2.5 volumes of ethanol. After 10 minutes at $-70°$ C., the DNA was recovered by centrifugation. The pellet was washed with 80% ethanol, dried and redissolved in $H_{13}O$ (0.5 ml). An aliquot (20 $A_{260}$ units) was lyophilized and redissolved in formamide (25 µl) containing 0.01% bromophenol blue. The sample was heated for 2 minutes at 90° C. and then analyzed on a 15% denaturing gel (1.6 mm thick). After electrophoresis for 16 hours at 350 V, products were visualized by UV shadowing. Oligonucleotides were eluted from the gel slices by soaking overnight in 0.5 M ammonium acetate, 0.01 M magnesium acetate, 0.1% sodium dodecylsulfate (SDS) (500 µl). The solution was filtered through 0.22 µm filters (Millipore) and the DNA recovered by ethanol precipitation. An aliquot of the purified oligonucleotide was analyzed on a denaturing gel after 5'-labelling with polynucleotide kinase and =P-ATP.

Assembly of Synthetic Duplexes

With the exception of the two 5'-terminal oligonucleotides, aliquots of oligonucleotides (100–500 pmoles) were lyophilized and then phosphorylated in a mixture (20 µl) containing 0.1 mM =P-ATP (5uCi/mMole), 50 mM Tris-HCl, pH 7.6, 20 mM dithiothreitol (DTT), 0.1 mM spermidine and 2 units of T4 polynucleotide kinase. After 60 minutes at 37° C. phosphorylated oligonucleotides were isolated by electrophoresis on 15% denaturing gels. Oligonucleotides were eluted from gel slices as described above. Recovery was determined by Cerenkov counting of aliquots. Phosphorylated oligonucleotides (50 pmoles) were annealed in groups of 5. The oligonucleotides were combined and lyophilized, dissolved in $H_2O$ (15 µl), heated to 90° C. for 5 minutes and then slowly cooled to 20° C. Then 10×ligase buffer, 200 mM DTT and 10 mM ATP were added to give a final concentration of 50 mM Tris-HCl, pH 7.4, 10 mM $MgCl_2$, 20 mM DTT, 0.5 mM ATP. T4 DNA ligase (0.5 µl) was added. After 60 minutes at 20° C. the products were ethanol precipitated and analyzed on 10% native gels. Products were eluted as described above and aliquots (1%) were analyzed on denaturing gels. Synthetic oligonucleotides of defined sequence were used as size markers (93-mer, 72-mer, 57-mer, 49-mer, 41-mer, 35-mer). Duplexes which contained products of the correct length were annealed at 50° C. and ligated together as described above. Products were isolated and analyzed in a similar manner.

Cloning of Synthetic Duplexes

All synthetic duplexes were initially cloned into the Cla I and Bam HI sites of pAT153 (plasmid pPA019 in FIG. 4). The vector was prepared by digestion with Cla I and Bam HI restriction endonucleases. After dephosphorylation with calf intestinal phosphatase (Boehringer), the 3.2 kbp fragment was purified by electrophoresis on a 1% agarose gel and recovered by electroelution.

Synthetic duplexes were phosphorylated before ligation to the vector. In a typical run, a 2:1 molar excess of vector:insert was used. Preparation of competent *E. coli* DHI cells, transformation of cells and selection of ampicillin resistant colonies was carried out as previously described by Hanahan, *J. Mol. Biol.* 166, 557–580 (1983) and Maniatis et al., *Molecular Cloning. A laboratory manual,* Cold Spring Harbor Lab., N.Y., (1982).

Colonies were innoculated into L-broth (7 ml) containing L-ampicillin (100 µg/ml, Sigma) and grown up overnight at 37° C. An aliquot was removed for a glycerol stock and DNA was isolated from the remainder of the culture by the method of Holmes and Quigley, *Anal. Biochem.* 114, 193–197 (1981). Colonies containing the insert were identified by restriction enzyme analysis and colony hybridization, using oligonucleotides present in the synthetic gene.

Plasmid DNA for sequence analysis was obtained from larger cultures (500 ml) grown in the presence of chloramphenicol. DNA was isolated by a modification of the method of Clewell and Helinski, *J. Bacteriology* 110, 1135–1146 (1972), and purified on CsCl gradients. The sequence of the synthetic inserts was confirmed by the Maxam-Gilbert method, *Methods in Enzymology* 65, 499–560 (1980).

A synthetic gene fragment coding for the natural signal sequence of t-PA (FIG. 2) was cloned into the ClaI - NdeI sites by methods described above.

Transfection

Monolayers of COS-7 cells (SV-40 transformed African green monkey kidney cells) [Gluzman, *Cell* 23, 175–182 (1981)] were grown in 6 well tissue culture dishes (Costar) at an innoculum of $2 \times 10^5$ cells/well in Dulbecco's modified Eagle's medium (DMEM) supplemented with 10% fetal calf serum (FCS; Flow). After 24 hours, the medium was aspirated and the monolayers were washed with serum free DMEM (3×). A solution of DEAE Dextran (Pharmacia, 400 µg/mL, 1 mL) containing expression vector (5 µg) was added to the monolayer and incubated for 30 minutes at 37° C. Cell monolayers were then washed twice with serum free medium and 100 µM clhoroquinine diphosphate in DMEM (1 ml) was added. After 3 hours the medium was aspiratd and the monolayers were washed with DMEM/2% FCS (3×). The cells were then incubated in DMEM/2% FCS (1 ml) for 48 hours. Cell monolayers were then washed with serum free DMEM and incubated for a further 24 hours in serum free medium (1 ml). The culture supernatant was removed and assayed for t-PA activity.

Construction of a Gene Coding for MB1012

The gene and protein sequences of MB1012 are shown in FIG. 3. The signal sequence starts at position −35 (as shown) with the mature protein beginning at +1. Some upstream and downstream DNA sequence is present.

A) Construction of pMON1386

The synthetic t-PA gene was obtained as a ClaI-BamH1 fragment cloned between the ClaI and BamH1 sites of the plasmid pAT153 (plasmid pPA0019 in FIG. 4). The 5'-ClaI site was converted to a BamH1 site by the use of BamH1 linkers. As outlined in FIG. 4, pPA019 was digested with ClaI and the resulting 5'-overhanging ends were converted to blunt ends with Klenow fragment of DNA polymerase. BamH1 linkers having the sequence 5'-CCGGATCCGG-3' (Pharmacia P-L Biochemicals) were then ligated onto these ends with T4 DNA ligase. After ligation the DNA was digested with BamH1 and the resulting 1710 bp t-PA fragment was isolated using NA-45 DEAE membrane as described in Schleicher and Schuell technical literature 364. The purified fragment was then ligated into the BamH1 site of the plasmid pML2. This mixture was used to transform *E. coli* HB101 cells to yield the plasmid pMON1386. Klenow fill-in reaction, ligation and transformation were done as described in Maniatis et al., *Molecular Cloning*, Cold Spring Harbor Lab., N.Y. (1982).

B) Construction of pMON9114 pMON1386 was digested with the enzymes StuI and Asp718 (an isoschizomer of KpnI) and treated with calf intestinal alkaline phosphatase to yield fragment 2 during the last half hour of digestion (FIG. 5). Oligonucleotides MB1012A, B, C and D were phosphorylated individually in ligation buffer containing 0.15 mM ATP, 5 µCi gamma-$^{32}$P-ATP (Amersham) with 5 units of T4 polynucleotide kinase and quantitated. 10 pmoles of each phosphorylated oligonucleotide were combined and annealed in the same buffer. The sequences of MB1012 A&C and MB1012 B&D, respectively, are as follows:

```
5'-CCTTGTATTTCTCTGACTTTGTCTGTCAATGTCCTGAGGGTTTTGCTGGTA-3'
3'-GGAACATAAAGAGACTGAAACAGACAGTTACAGGACTCCCAAAACGACCATTCACAACA-5'

5'-AGTGTTGTGAAATTGATGGGAATTCTGACTGTTACTTTGGTTCTGGTTCTGCTTACAGAG-3'
3'-CTTTAACTACCCTTAAGACTGACAATGAAACCAAGACCAAGACGAATGTCTCCATG-5'
```

The fragment 2 was ligated with synthetic oligonucleotide fragments MB1012 A&C and MB1012 B&D (fragment 3 in FIG. 5) in ligation buffer (25 mM Tris-HCl, pH 8.0, 10 mM MgCl$_2$, 2 mM spermidine and 10 mM dithiothreitol) containing 1 mM ATP using 1 unit of T4 DNA ligase. After 16 hrs ligation at 18° C. the ligation mixture was used to transform competent *E. coli* JM109 cells as described in Davis et al., *Advanced Bacterial Genetics*, Cold Spring Harbor Laboratory, N.Y. (1980). The resulting plasmid was named pMON9114 (FIG. 5). Since digested pMON1386 was treated with alkaline phosphatase, religation of the deleted 379 bp StuI to Asp718 fragment with the fragment 2 was not expected. However, to prevent a low level of background which may occur due to small amount of religation the ligated DNA was digested with Sac2 prior to transformation. Sac2 occurs only in the 379 bp fragment which is deleted from pMON1386 during the digestion with StuI /Asp718.

C) Construction of pMON9115

Plasmid pMON9115 containing the sequence for t-PA variant MB1012 was constructed from pMON9114 and synthetic oligonucletide fragment LES 5&6(see FIG. 6). The sequence of LES 5&6 is as follows:

```
5'CTGTTCTGAAGGTAACTCTGACTGTTACTTCGGTAACGGTTCTGCTTACAGAGGTAC-3'
3'-GACAAGACTTCCATTGAGACTGACAATGCCGCCATTGCCAAGACGAATGTCTC-5'
```

Plasmid pMON9114 was linearized with Kpn1 and not treated with alkaline phosphatase. Fragment 2 in FIG. 6A was ligated with unphosphorylated annealed synthetic oligonucleotide fragment LES 5&6 (fragment 3 in FIG. 6A) in ligation buffer (25 mM Tris-HCl, pH 8.0, 10 mM MgCl$_2$, 2 mM spermidine and 10 mM dithiothreitol) containing 1 mM ATP using 1 unit of T4 DNA ligase. Ligated DNA mixture was digested with XbaI and the resulting 800 bp Pvu2 to Xba1 fragment (fragment 5 in FIG. 6B) was separated on 5% acrylamide gel and purified by electroelution. Plasmid pMON9114 was digested with enzymes Pvu2 and Xba1. The fragment 7 in FIG. 6B was isolated using NA-45 DEAE membrane as described in section A, except the DNA was eluted with 5 M ammonium acetate in 20 mM Tris-HCl, pH 8.0. Fragment 7 was ligated with fragment 5 as described above and the ligation mixture was used to transform *E. coli* JM109 cells as described in section B. The resulting plasmid pMON9115 (4321 bp) carries the coding sequences for t-PA variant MB1012.

Expression of MB1012

The t-PA variant MB1012 BamH1 fragment was isolated from pMON9115 by digestion of this plasmid with BamHI and purification of the insert fragment by electrophoresis on an agarose gel. The MB1012 BamHI fragment was then inserted into the unique BamHI site of the expression vector pMON1123 by reaction with T4 ligase using standard conditions [Maniatis et al. *Molecular Cloning*, Cold Spring Harbor Laboratory, N.Y. (1982). The pMON1123 expression vector is based on the plasmid pPBV2308 (a gift of Dr. Dean Hamer, National Institutes of Health). The latter plasmid contains specific parts of the bovine papilloma virus (BPV) and part of plasmid pML2. pMON1123 was constructed by insertion of DNA fragments encoding the mouse metallothionien I promoter and the SV40 Late poly A addition site in such a way that these two fragments are separated by a unique BamHI site. DNA fragments inserted into this BamHI site are therefore expressed using the metallothionien promoter and SV40 Late poly A site regulatory signals. Insertion of the MB1012 BamHI fragment into pMON1123 yielded the plasmid pMON1437 (FIG. 7).

C-127 cells (mouse mammary tumor cells) (ATCC CRL 1616) were grown in high glucose Dulbecco's modified Eagles medium (DMEM) containing 5% heat-inactivated fetal bovine serum, 1× penicillin-streptomycin, and 1× glutamine. Twenty four hours prior to transfection, cells were seeded in 60 mm dishes at 4×10$^6$ cells per dish. Cells were cotransfected with a mixture of pMON1437 and pSV2neo [Southern and Berg, *J. Molec. Appl. Genet.* 1, 327–341 (1982)] by the calcium phosphate precipitate method of Wigler et al, *Cell* 16, 777 (1979). Twenty four hours after transfection the 60 mm plates were each split 1:10 into 100 mm dishes containing high glucose DMEM, 5% heat-inactivated fetal bovine serum, 1× penicillin-streptomycin, 1×glutamine, and 50 KIU of aprotinin. This media was also supplemented with 800 µg/ml of the antibiotic G418 (genticin) (GIBCO) for selection of neomycin resistant transfectants [Southern and Berg, supra]. After two weeks of selection G418 resistant colonies appeared. These colonies were screened for MB1012 production by the use of a fibrin overlay screen performed essentially by the method of Cederholm-Williams et al., in "Treatment of Metastasis: Problems and Prospects," Hellman and Eccles, Eds. (Taylor and Francis, London and Philadelphia) pp. 347-350 (1985). Each plate was overlayed with a 1.2% agarose matrix containing Dulbecco's minimal Eagles medium, 0.1 U/ml bovine thrombin (CalBiochem), 3 mg/ml bovine fibrinogen (CalBiochem), and 0.07/ml human plasminogen (Kabi). Following incubation at 37° C. clearing zones in the fibrin matrix appeared over specific colonies. These colonies were picked and seeded into wells of 24 well plates. Each well was allowed to grow to confluency and then expanded into a T75 flask to establish a stable line. The expression level of these lines was monitored by a t-PA specific ELISA (American Diagnostica).

The cell line having the highest expression levels was expanded into multiple T75 flasks. These cells were used to seed a 6000 cm$^2$ cell factory (Nunc). The cells were allowed to proliferate in the normal growth media until confluent. At this time the cells were washed with phosphate buffered saline containing Ca$^{+2}$ and Mg$^{+2}$ and were then fed with serum-free DMEM containing 2×penicillin-streptomycin, 1×glutamine, 50 KIU/ml aprotinin, and 0.3% lactalbumin hydrolysate. Conditioned media was replaced with fresh media every 3 days and used for protein purification.

MB1012 Isolation

Purification of MB1012 was achieved by affinity chromatography on an Erythrina inhibitor-Sepharose® 4B column [Heussen et al, *J. Biol. Chem.* 259, 11635-11638 (1984)]. The conditioned medium was concentrated by ultrafiltration on Amicon's YM 30 spiral membrane system. The concentrates were made up to 0.5 M NH$_4$HCO$_3$, 1% Triton X-100 and centrifuged at 26,000 ×g for 1 hr. The supernatant was then loaded onto an Erythrina inhibitor-Sepharose 4B column (6 ×2.5 cm). The column was washed with 300 ml of 0.5 M NH$_4$HCO$_3$, 1% Triton X-100 and then with 50 mM NH$_4$HCO$_3$ until detergent free. The bound MB1012 was then eluted with 2.5 M KSCN, 50 mM Na$_3$PO$_4$, pH 7.3. The eluted MB1012 was then dialyzed extensively against 1 M NH$_4$HCO$_3$. The whole purification process was carried out at 4° C.

Amino Acid Sequence Analysis

Automated Edman degradation chemistry was used to determine the NH$_2$-terminal protein sequence. An Applied Biosystems, Inc., model 470A gas phase sequencer (Foster City, Calif.) was employed for the degradation [Hunkapiller et al., *Methods Enzymol* 91, 399-413 (1983)]. The respective PTH-aa derivatives were identified by RP-HPLC analysis in an on-line manner employing an Applied Biosystems, Inc., Model 120A PTH Analyzer fitted with a Brownlee 2.1 mm I.D. PTH-C18 column.

Protein Determination

The protein concentration of MB1012 was determined by measuring absorbance at 280 nm and assuming that a concentration of 1 mg/ml gives an absorbance of 1.75.

Assays of Enzymatic Activity

The amidolytic activity of MB1012 was measured using a synthetic substrate, S-2288 (H-D-isoleucyl-L-propyl-L-arginine-p-nitroanilide). The reaction mixture contains 10 μl of 20 μg/ml MB1012 in PBS, 5 mg/ml BSA, 2.5 mg/ml bovine gamma globulin, 10 μl of 0.01M S-2288, and 230 μl of 0.1 M Tris-HCl, pH 8.7, 0.5% Triton X-100. Amidolysis was followed by measuring the absorbance change with time at 405 nm.

The plasminogen activator activity of MB1012 was determined by a parabolic rate assay system as follows: Standard t-PA (0-15 I.U/ml) or MB1012 were prepared in a PBS solution containing 5 mg/ml BSA and 2.5 mg/ml bovine gamma globulin (PBB). Twenty μl of the t-PAs were mixed with 20 μl of human fibrinogen (2 mg/ml in 0.15 M NaCl) in microfuge tubes and placed on ice. To each tube was added 60 μl of a reaction cocktail which consisted of 20 μl of P-buffer (0.25 M Tris-HCl, pH 7.35, 0.5 M NaCl, 25 mM EDTA), 5 μl of 3 mg/ml plasminogen, 5 μl of S-2251 (H-D-Val-Leu-Lys-p-nitroanilide), 5 μl of 20 U/ml human thrombin, 1 mg/ml BSA, and 25 μl H$_2$O. These were kept on ice until the cocktail was added to all the tubes. The tubes were then transferred to a water bath and incubated at 37° C. for 1.5 hr. To stop the reaction, 0.2 ml of 10% acetic acid was added to each tube. After a brief vortexing and centrifugation, the supernatants were transferred to a 96-well plate for absorbance measurement at 410 nm using a control (without added t-PA) as reference. The activities of the t-PA variants were determined by comparing the A$_{410}$ with those of standard t-PA.

In this assay, it was found that a batch of melanoma single-chain t-PA obtained from American Diagnostica (lot 47-10) has a specific activity of 769.+21 I.U./ug using WHO t-PA standards as reference. Because of limited supply of WHO standard, American Diagnostica's t-PA (lot 47-01) was subsequently used as the standard.

Plasma Clot Lysis Assay

The standard t-PA and MB1012 induced plasma clot lysis assay was performed essentially as described by Wun and Capuano, *J. Biol. Chem.* 260, 5061-5066 (1985). In brief, plasma was supplemented with $^{125}$I-fibrinogen and 0.02% NaN$_3$. Ten μl of a solution of the standard t-PA or MB1012 and 5 μl of 100 NIH units/ml of thrombin were added to a microfuge tube. To this was added 85 μl of the plasma, followed by incubation on ice for 15 minutes and then at 37° C. for 4 hours. The tube was then taken, vortexed and centrifuged to remove insoluble fibrin. The percent of clot lysis was calculated based on the amount of $^{125}$I- fibrin degradation products released into serum.

Preparation of $^{125}$I-t-PAs

Iodination of t-PAs was carried out by a modified chloramine T method. Ninety μl of MB1012 (1.1 mg/ml) was mixed with 5 μl of $^{125}$I- NaI (0.5 mCi) and incubated on ice for 30 min. Then, the mixture was chromatographed on a 5 ml Sephadex® G25 (fine) column pre-equilabrated in 1 M NH$_4$HCO$_3$. Fractions of 0.2 ml were collected and the radioactive protein peak was pooled.

In Vivo Clearance of t-PAs in Rat

Wistar rats (~300 g) were anesthetized by intraperitoneal injection of sodium pentobarbital. The rat was then cannulated at the right jugular vein and carotid artery using polyethylene tubing (I.D. 0.58 mm; O.D. 0.97 mm). The cannula of the carotid artery was connected to silicon tubing (I.D. 0.63 mm; O.D. 1.2 mm) which fed through a larger tubing (I.D. 1.3 mm; O.D. 3.3 mm) of a microperpex peristaltic pump (LKB). Blood was collected into a fraction collector. A heparin solution was injected through the jugular vein such that the concentration in circulation was approximately 2 units/ml, assuming that the blood volume is 7 ml per 100 g body weight. After 5 min., 15 μg of $^{125}$t-PA was injected through the jugular vein and the blood was pumped into fraction collector at a speed of 30 μl/fraction/20 sec initially, and at 30 μl/fraction/60 sec after 25 fractions were collected. The time course of the clearance of MB1012 is followed by counting the radioactivity in each fraction of blood collected. Half-life of MB1012 was calculated by linear regression of ln (t-PA) vs. time. The half-life (t½) was calculated from the formula $$t_{\frac{1}{2}} = \frac{\ln 0.5}{S},$$

S being the slope of the regression line.

Assay Results

Isolation of MB1012

The C-127 cells transfected with MB1012 gene were grown in culture and the serum-free conditioned medium was collected for purification of MB1012 using Erythrina inhibitor Sepharose 4B as described above. From 1 L of medium, 4 mg of MB1012 was isolated.

Enzymatic Activity of MB1012

The enzymatic properties of the MB1012 were assessed by a number of assays and compared to melanoma t-PA (MB1022). In the amidolytic assay system described above, MB1022 t-PA gave an activity of 0.014, while that of MB1012 gave an activity of 0.028.

In the parabolic rate assay, consisting of fibrin-plasminogen-S2251 and t-PAs, the MB1022 possesses a specific activity of 769 I.U./μg. In comparison, the MB1012 has a specific activity of 253 I.U./μg.

In the plasma clot lysis assay, the concentration of MB1012 required to lyse 50% of the clot in 4 hr at 37° C. is 108 ng/ml, in comparison to that for MB1022 t-PA which requires 17 ng/ml. These in vitro data suggest that MB1012 has 4-6 fold decrease in fibrin-specific activity compared to MB1022 t-PA.

Clearance of MB1012 in the Rat

As shown in FIG. 8, the clearance of melanoma t-PA MB1022 in the rat after bolus injection follows biphasic kinetics with an initial rapid decline (t½ alpha=4.4 +/−0.1 min, n=3) followed by a slower decline (t½ beta=19+/−3 min, n=2). In comparison, MB1012 shows an t½ alpha=8.4 min and t½ beta=26.9 min. (FIG. 9).

The modified t-PA of the invention can be used for the treatment of thrombolytic conditions by suitable administration to a patient in need of such treatment. The amount of the t-PA which would normally be administered is primarily dependent upon the physical characteristics of the recipient and the severity of the thrombolytic condition. The amount to be administered must be an effective amount, that is, an amount which is medically beneficial but does not present toxic effects which overweigh the advantages which accompany its use. The preferable route of administration is parenteral, especially intravenous. Intravenous administration of the t-PA in solution with normal physiologic saline is illustrative. Other suitable formulations of the active t-PA in pharmaceutically acceptable diluents or carriers in therapeutic dosage form can be prepared by reference to general texts in the pharmaceutical field such as, for example, *Remington's Pharmaceutical Sciences*, Ed. Arthur Osol, 16th ed., 1980, Mack Publishing Co., Easton, Pa.

Various other examples will be apparent to the person skilled in the art after reading the present disclosure without departing from the spirit and scope of the invention and it is intended that all such other examples be included within the scope of the appended claims.

What is claimed is:

1. A modified human tissue plasminogen activator having the amino acid sequence of the mature modified human tissue plasminogen activator as shown in FIG. 3A–C.

2. A DNA molecule encoding the modified human tissue plasminogen activator of claim 1.

3. A t-PA gene having the nucleotide sequence as shown in FIG. 3A–C.

4. A cloning vector comprising the DNA molecule of claim 2.

5. A cloning vector comprising the gene of claim 3.

6. Plasmid pMON1437.

7. Mouse C-127 cells transformed with the plasmid of claim 6.

8. A process for preparing the modified human tissue plasminogen activator of claim 1 which comprises culturing under conditions sufficient to produce said tissue plasminogen activator a suitable eukaryotic host cell which has been transformed with a replicable expression vector comprising the DNA coding for said tissue plasminogen activator and whereby said plasminogen activator has an improved half-life compared to native human tissue plasminogen activator.

9. A pharmaceutical composition comprising the modified human tissue plasminogen activator of claim 1, and a pharmaceutically acceptable diluent or carrier.

* * * * *